(12) United States Patent
Castillo (10) Patent No.: US 10,494,421 B2
(45) Date of Patent: *Dec. 3, 2019

(54) SYSTEM, APPARATUS AND METHOD FOR BIOMOLECULES PRODUCTION

(71) Applicant: UNIVERCELLS NV, Etterbeek (BE)

(72) Inventor: José Castillo, Brussels (BE)

(73) Assignee: UNIVERCELLS NV, Gosselies (BE)

( * ) Notice: Subject to any disclaimer, the term of this patent is extended or adjusted under 35 U.S.C. 154(b) by 177 days.

This patent is subject to a terminal disclaimer.

(21) Appl. No.: 15/117,691

(22) PCT Filed: Feb. 9, 2015

(86) PCT No.: PCT/EP2015/052617
§ 371 (c)(1),
(2) Date: Aug. 9, 2016

(87) PCT Pub. No.: WO2015/118146
PCT Pub. Date: Aug. 13, 2015

(65) Prior Publication Data
US 2016/0355572 A1  Dec. 8, 2016

(30) Foreign Application Priority Data
Feb. 10, 2014 (EP) .................... 14154418

(51) Int. Cl.
*C07K 16/10* (2006.01)
*C12M 1/00* (2006.01)
*C12M 1/16* (2006.01)
*C12M 1/40* (2006.01)

(52) U.S. Cl.
CPC ......... *C07K 16/1027* (2013.01); *C12M 21/14* (2013.01); *C12M 21/18* (2013.01); *C12M 23/52* (2013.01); *C12M 29/04* (2013.01); *C12M 29/10* (2013.01); *C12M 47/12* (2013.01); *C07K 2317/14* (2013.01)

(58) Field of Classification Search
CPC ......... C12M 41/48; C12M 1/00; C12M 1/12; C12M 1/34; C12M 1/36; C12M 21/14; C12M 21/18
See application file for complete search history.

(56) References Cited

U.S. PATENT DOCUMENTS

| 4,839,284 | A | 6/1989 | Kern et al. |
|---|---|---|---|
| 6,139,746 | A | 10/2000 | Kopf |
| 7,264,923 | B2 | 9/2007 | Virgin et al. |
| 8,455,219 | B2 | 6/2013 | Hsieh |
| 8,540,499 | B2 | 9/2013 | Page et al. |
| 2007/0249032 | A1 | 10/2007 | Pang et al. |
| 2009/0042253 | A1 | 2/2009 | Hiller |
| 2011/0182901 | A1 | 7/2011 | Peter et al. |
| 2011/0207223 | A1 | 8/2011 | Tang et al. |
| 2012/0231500 | A1 | 9/2012 | Daramola et al. |
| 2013/0059383 | A1 | 3/2013 | Dijkhuizen Borgart et al. |
| 2013/0071872 | A1 | 3/2013 | Ho et al. |
| 2014/0193901 | A1 | 7/2014 | Lee et al. |
| 2018/0030398 | A1* | 2/2018 | Castillo .................. C12M 23/40 |

FOREIGN PATENT DOCUMENTS

| AU | 2003261189 A1 | 2/2004 |
|---|---|---|
| AU | 2013203995 A1 | 5/2013 |
| CN | 101864361 A | 10/2010 |
| CN | 104762251 | 7/2015 |
| EP | 485689 A1 | 5/1992 |
| EP | 550553 A1 | 7/1993 |
| EP | 576049 A1 | 12/1993 |
| EP | 728202 A1 | 8/1996 |
| EP | 754237 A1 | 1/1997 |
| EP | 829535 A1 | 3/1998 |
| EP | 979297 A1 | 2/2000 |
| EP | 1007713 A2 | 6/2000 |
| EP | 1034290 A1 | 9/2000 |
| EP | 1135025 A1 | 9/2001 |
| EP | 1175931 A1 | 1/2002 |
| EP | 1326990 A2 | 7/2003 |
| EP | 1402023 A2 | 3/2004 |
| EP | 1430116 A2 | 6/2004 |
| EP | 1461441 A1 | 9/2004 |
| EP | 1633877 A1 | 3/2006 |
| EP | 1642982 A1 | 4/2006 |
| EP | 1651666 A1 | 5/2006 |
| EP | 1664312 A1 | 6/2006 |

(Continued)

OTHER PUBLICATIONS

"Mobius CellReady 50L and 200L Single Use Bioreactor Systems", Performance Guide, www.emdmillipore.com/offices, 2012 (Year: 2012).*

McGlothlen et al., Proceedings 2013, 7 (supple 6): P95, http:www.biomedcentral.com/1753-6561/7/S6/P95, "Use of microcarriers in Mobius CellReady bioreactors to support growth of adherent cells" (Year: 2013).*

Choo, Chiou-Yu et al., "High-level Production of a Monoclonal Antibody in Murine Myeloma Cells by Perfusion Culture Using a Gravity Settler," *Biotechnology Progress*, vol. 23(1), pp. 225-231 (Jan. 31, 2007).

(Continued)

*Primary Examiner* — Ruth A Davis (57) ABSTRACT

An automated method for the production of cells and/or biomolecules such as protein or peptides includes culturing cells in at least one high cell density bioreactor, thereby fluidly connecting said bioreactor with a culture medium supply and a gas or gaseous mixture; fluidly connecting said bioreactor with a downstream unit; and growing cells to a density at least 50 million cells per ml. The total volume of the bioreactor is at least 10 liters. A system suitable for implementation of the automated method above is a small-scale and cupboard-sized system, which can be placed in a portable clean room.

9 Claims, 5 Drawing Sheets

(56) References Cited

FOREIGN PATENT DOCUMENTS

| | | |
|---|---|---|
| EP | 1851319 A1 | 11/2007 |
| EP | 1942182 A2 | 7/2008 |
| EP | 1997900 A2 | 12/2008 |
| EP | 2035557 A2 | 3/2009 |
| EP | 2045330 A1 | 4/2009 |
| EP | 2066346 A2 | 6/2009 |
| EP | 2162665 A1 | 3/2010 |
| EP | 2183368 A2 | 5/2010 |
| EP | 2331557 A1 | 6/2011 |
| EP | 2346984 A2 | 7/2011 |
| EP | 2404991 A2 | 1/2012 |
| EP | 2562258 A1 | 2/2013 |
| EP | 2563909 A1 | 3/2013 |
| EP | 2578229 A1 | 4/2013 |
| JP | 2014158461 A | 9/2014 |
| TW | 200526775 A | 8/2005 |
| TW | 200700552 A | 1/2007 |
| WO | WO1991002793 | 3/1991 |
| WO | WO1999027123 | 6/1999 |
| WO | WO 00/46354 A1 | 8/2000 |
| WO | WO2003083065 | 10/2003 |
| WO | WO2006046243 A1 | 5/2006 |
| WO | WO 2007/071072 A1 | 6/2007 |
| WO | WO2010122094 A1 | 10/2010 |
| WO | WO2011051267 A1 | 5/2011 |
| WO | WO2011098484 A1 | 8/2011 |
| WO | WO 2012/171030 A2 | 12/2012 |
| WO | WO2012171030 A2 | 12/2012 |
| WO | WO 2014/001261 A1 | 1/2014 |

OTHER PUBLICATIONS

Su, Wei Wen et al., "Continuous Plant Cell Perfusion Culture: Bioreactor Characterization and Secreted Enzyme Production," *Journal of Bioscience and Bioengineering*, vol. 95(1), pp. 13-20 (Jan. 31, 2003).

* cited by examiner

SYSTEM, APPARATUS AND METHOD FOR BIOMOLECULES PRODUCTION

INCORPORATION BY REFERENCE TO ANY PRIORITY APPLICATIONS

This application is the U.S. National Phase of International Application No. PCT/EP2015/052617, filed Feb. 9, 2015, designating the U.S. and claiming priority to European Application No. 14154418.9, filed Feb. 10, 2014. Any and all applications for which a foreign or domestic priority claim is identified here or in the Application Data Sheet as filed with the present application are hereby incorporated by reference under 37 CFR 1.57.

FIELD OF THE INVENTION

The invention pertains to methods and systems for the production and/or the purification of cells or cell products, such as proteins or peptides. More in particular, the invention provides methods and systems for antibodies production.

BACKGROUND OF THE INVENTION

With the increased use of proteins, such as antibodies, in clinical diagnostics and therapy, the need has arisen for more efficient, rapid, sterile production and purification methods.

Conventional approaches and tools for manufacturing cells or cell based products typically involve numerous manual manipulations that are subject to variations even when conducted by skilled technicians. Small quantities of cell-secreted product are produced in different ways. T-flasks, roller bottles, stirred bottles or cell bags are manual methods using incubators or warm-rooms to provide environments for cell growth and production. These methods are very labor intensive, subject to mistakes and difficult for large-scale production.

Production of cell secreted products can be achieved using a bioreactor (fibers, microfibers, hollow fiber, ceramic matrix, fluidizer bed, fixed bed, etc.) or using a stirred tank. This increases product concentration. The systems currently available are general purpose in nature and require considerable time from trained operators to setup, load, flush, inoculate, run, harvest, and unload.

Prior art techniques use a large-scale set-up wherein cells are being grown in batch bioreactors of e.g. 10000 liters (L). After a cultivation period, the antigens or antibodies of the batch are harvested within about 8 hours. Hereby, the 10000 L of suspension is clarified, the medium is exchanged (cell-culture medium replaced by buffer medium) by diafiltration, and the compounds are separated or purified by chromatography. A further filtration step may follow. The disadvantages of the prior art technique include the use of a big filter, a large amount of buffer medium, a large chromatography column and a considerable necessary amount of purified water. These amounts represent a considerable cost in terms of purified water production and water storage. A major disadvantage is the yield loss in the clarification step which is an essential step of this set-up for obtaining a diafiltration which is efficient enough to exchange the cell-culture medium within the limit of 8 hours.

Another drawback of the current available systems is the large investments that are required in terms of necessary installations, necessary space, etc. (the 'hardware') but also in terms of necessary material to produce the desired biomolecules. In addition, the necessary input of energy weighs tremendously on the required budget. Consequently, the huge investments to be made put a restrain on further development in the field of therapeutic antibody production, not only in the US and Europe, but also in the developing countries.

WO 2012/171030 describes an automated integrated system comprising a cell growth unit and purification unit. The system is still quite demanding in use and requires further optimization measures to improve ease of use and to increase output especially that said system is not scalable.

Accordingly, there is a need for systems and methods whereby cells and/or cell products can be cultured and if desired purified in a fully automated, rapid and sterile manner. Furthermore, there is a need in a methodology and system that provides a high product output with minimal investment cost and lowered capital expenditures (CAPEX) and operating expenditures (OPEX).

It is the aim of the current invention to provide methods and systems for the production of cells and/or cell products which overcome at least part of the above mentioned drawbacks and disadvantages. One object of the invention is to provide automated and integrated methods and systems for the growth and maintenance of cells but also for variable multiple downstream applications such as harvest and/or purification of cells and/or cell products (for instance, proteins or peptides).

SUMMARY OF THE INVENTION

In a first aspect, the present invention provides an integrated automated method for the production of biomolecules such as protein or peptides comprising the steps of culturing cells in at least one high cell density bioreactor, thereby fluidly connecting said bioreactor with a culture medium supply and a gas or gaseous mixture; fluidly connecting said bioreactor with a downstream unit; and growing cells to a density at least 50 million cells per ml. Preferably, the bioreactor total volume is at least 10 liters. In a preferred embodiment, the produced biomolecules are antibodies.

In a second aspect, the present invention provides a system suitable for the implementation of the method of the invention. The system is a small-scale cupboard-sized system and can be placed in a portable clean room. In a preferred embodiment, the invention provides a system for the production of biomolecules such as proteins or peptides, comprising a cell culturing unit and a downstream unit which are fluidly connected to each other. Said cell culturing unit comprises at least one perfusion bioreactor, which allows growing cells at a density of at least 50 million cells per ml, and supply means for supplying said bioreactor with cell medium and gas or gaseous mixture. The system is characterized in that the bioreactor total volume is at least 10 liters. In a preferred embodiment, the produced biomolecules are antibodies.

Conventionally, in order to manage the production of a large amount of therapeutic products such as antibodies, a considerable number of large instruments (such as large bioreactors, large filters, large purifications chromatography columns, etc) is needed. Compactness of the design and the amount of support resources has however become an important issue. To support large units becomes a logistics problem for the system. The system of the present invention has no such requirement in particular thanks to the use of a small size bioreactor and the further processing of pre-defined small volume of supernatant. The present method and system are devoid of manual handling, thereby considerably reducing contamination risk.

Cell products such as antibodies are presently being produced in large-scale facilities. Cells are usually cultured for about 20 days in a considerable volume of culture medium of about 10000 L. Afterwards, cell culture is stopped and the considerable volume of culture medium is then treated to extract the desired molecule. Said facilities are rather expensive and their cost is about $100 million.

The present invention provides methods and systems wherein cells are cultured at high density. Preferably, said high density culture is carried out in a continuous perfusion small size bioreactor. More preferably, high density culture is maintained in the bioreactor. The systems and the methods of the invention provide for an automated, integrated and continuous chain of operations starting from cells growth until obtaining the desired product which can be cells or cells products such as proteins or peptides. In a preferred embodiment of the invention, after reaching a predefined cell density inside the bioreactor, a pre-defined small volume of supernatant is further processed in the downstream unit of the system. Processing of the supernatant, in pre-defined small volume, is carried out while maintaining the high cell density culture inside the bioreactor. By supernatant, reference is made to the culture medium which is inside the bioreactor during cell culture.

Amongst the advantages of systems and methods of the invention is to provide for high yield cells and/or cell products production compared to the methods and the systems of the prior art thereby reducing costs of the final product. The systems and methods of the invention also allow production of cells and/or cell products using a significantly smaller amount of purified water than prior art systems and methods. The present invention provides cheaper fully-automated and integrated systems, which cost is at least 5 to 6 times less than the usual large-scale systems. This eventually results in a lower investment and production cost, which is a considerable advantage, e.g. when aiming at manufacturing for third-world countries. The invention allows providing third-world countries with national production systems and also enables pharmaceutical companies without biotech background to produce cell products such as antibodies in bulk.

DETAILED DESCRIPTION OF THE INVENTION

The present invention concerns a method and system for the production of cells and/or cell products or biomolecules such as proteins or peptides (e.g. antibodies). The invention specifically aims to provide a method with an optimal efficiency in terms of input of material and products output. The current invention thereto aims to provide a fully integrated and automated methodology and system for the production of cells and/or biomolecules. By "proteins or peptides" and "cells and/or biomolecules" reference is made to antibodies as well as antigens.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In a first aspect, the present invention provides an integrated automated method for the production of biomolecules such as proteins or peptides. More in particular, the invention provides a method for antibody production. In a preferred embodiment, the method of the invention is suitable to be carried out by a system comprising a cell culture unit and a downstream unit. The cell culture unit comprises at least one bioreactor for cell growth and/or cells products production. The downstream unit may comprise different components or means suitable for further processing the supernatant, cultured cells and/or cells products.

By preference, the method of the current invention comprises the steps of culturing cells in at least one high cell density bioreactor, thereby fluidly connecting said bioreactor with a culture medium supply and a gas or gaseous mixture; fluidly connecting said bioreactor with a downstream unit; and growing cells to a density at least 50 million cells per ml. Preferably, the bioreactor total volume is at least 10 L. At least one sensor is preferably provided for measuring the cell density inside the bioreactor.

In a preferred embodiment, the bioreactor total volume is at least 10 L, preferably at least 20 L, more preferably at least 30 L, even more preferably at least 40 L, most preferably at least 50 L. The bioreactor total volume is at most 1000 L, preferably at most 900 L, more preferably at most 800 L, even more preferably at most 700 L, most preferably at most 500 L, even most preferably 500 L. In a further preferred embodiment, the bioreactor total volume is at most 400 L, preferably at most 300 L, more preferably at most 250 L, most preferably at most 100 L. By bioreactor total volume reference is made to the total liquid volume that can be introduced in the bioreactor, which will then be full.

Preferably, the culture medium volume provided to the bioreactor for culturing cells is sufficient to fill about half of the total volume of said bioreactor. For instance, if the bioreactor total volume is 1000 L then 400 to 700 L, preferably 450 to 600 L, more preferably 480 to 500 L or any value comprises in the mentioned ranges is provided to the bioreactor for culturing cells. Preferably, for antibodies production, the bioreactor comprises at least 80 L, preferably at least 90 L, more preferably at least 100 L of culture medium and at most 200 L, preferably at most 180 L, more preferably at most 150 L, even more preferably at most 140 L and most preferably about 125 L of culture medium.

In a preferred embodiment, cells (mammalian or insect cells) and adapted culture medium are introduced in the bioreactor. Adapted culture medium refers to the composition of the medium which is required for the growth of the cells. Said compositions are known to the person skilled in the art and generally comprise salts, vitamins, amino acids, sugars or any combination thereof. The culture medium is preferably provided to the bioreactor from an external culture medium container, i.e. not contained in the system of the invention. From said external container, the culture medium is directed to an internal culture medium tank, i.e. positioned inside the system. Preferably, the culture medium is preheated prior being provided to the bioreactor. More preferably, the culture medium is heated in the internal culture medium tank. The preheat temperature of the culture medium is of from 20 to 40° C., preferably from 25 to 38° C., more preferably from 30 to 37° C. In a most preferred embodiment, said culture medium is pre-heated at about 37° C.

In a preferred embodiment, a waste collection container, into which metabolic wastes are being removed from the bioreactor, is provided. Such containers and the required connections for ensuring waste removal are known to the person skilled in the art.

In a preferred embodiment, a mixture of culture medium and gas, such as pure oxygen, or a mixture of culture medium and gaseous mixture comprising oxygen are provided to the bioreactor through one single supply line or through one inlet of said bioreactor. The use of one single supply line simplifies the setup of the system and method as it reduces the number of required connections and tubings.

Cells require oxygen during their growth phase in order to have an optimal growth. The bioreactor can be subject to motioning, thereby increasing oxygen transfer by a factor of at least 10 compared to conventional methods. Operation of the bioreactor at gas equilibrium is hence achieved. This on its turn increases cell growth, which has a positive impact on the biomolecule production. Also, when operating at constant gas equilibrium, all control units or sensory devices may be omitted, providing a straightforward and simple methodology. In addition, sensor failure is no longer an issue, and repairs which were needed in prior art systems due to said sensor failure are not necessary anymore, leading to a high reduction in operation and personnel costs. Motioning the bioreactor may include, but is not limited to rotating along a horizontal axis, rotating along a vertical axis, a rocking motion along a tilted or inclined horizontal axis of the bioreactor or any combination thereof.

In a preferred embodiment, cells are cultured in the bioreactor for a time period which can vary from few hours to several days depending on the cultured cells. The culture time period is at least 4 hours, at least 10 hours, at least 24 hours, at least 5 days at least 7 days or any time in-between. The culture time period is at most 70 days, at most 60 days, at most 50, at most 40 days, at most 25 days, at most 20 days, at most 10 days or any time in-between.

Depending on the final product, viral transduction or introduction of viral vectors can be utilized. Viral replication competent vectors or replicons have been used for a long time as an alternative expression system to increase the yields of therapeutic proteins in mammalian cells. The target gene(s) can be expressed under transcriptional control of viral promoters whereby the mRNAs accumulate to extremely high levels in the cytoplasm after transfection and upon replication, yielding large amounts of target protein. The viral infection can lead to a transduction process without lysis of the cultured cells or to the lysis of the cultured cells thereby bringing the cells content into the supernatant of the bioreactor.

Alternatively, hybridoma cells or stably transfected cells can be cultured in order to produce the desired protein or peptide such as an antibody or an antibody fragment.

Examples of viral replication systems include but are not limiting to polyoma viruses, lentiviral systems, retroviral systems, adenoviral systems, adeno-associated viruses. Examples of preferred cells used in the current system include but are not limited to Vero cells, Hek293T cells, COS cells, CHO cells.

Figure 2:
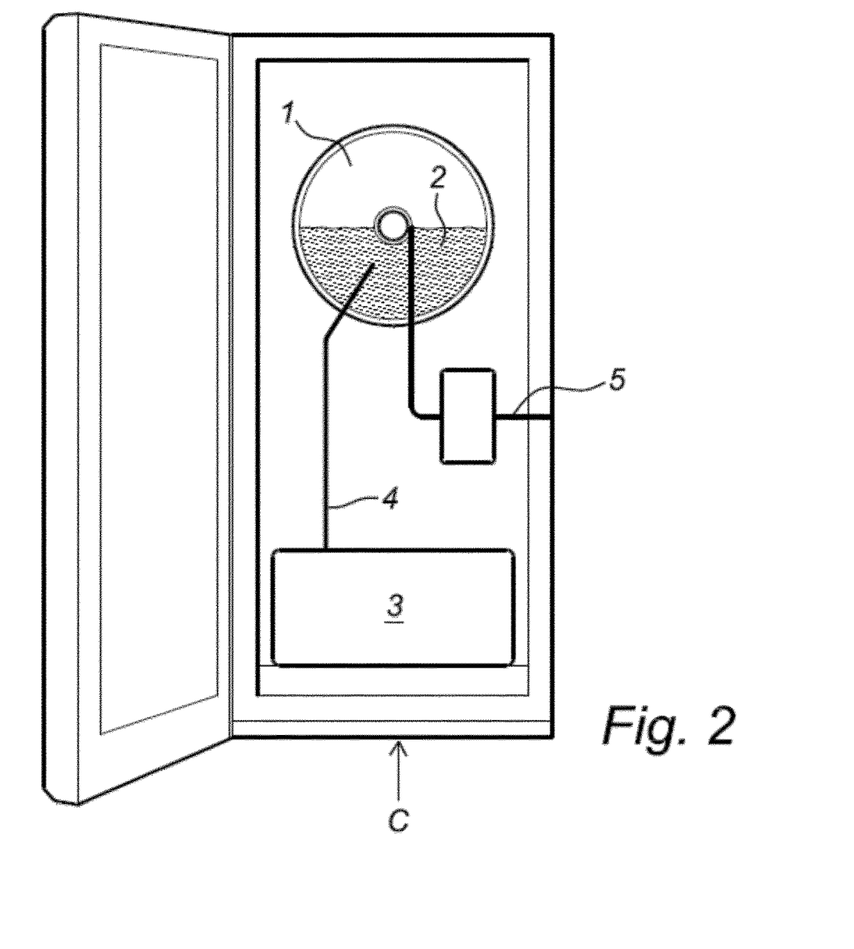
FIG. 2 shows an embodiment of the cell culture unit of the invention.

In a preferred embodiment of the current invention, bioreactor's supplemented medium is transferred from the bioreactor to or harvested into the downstream unit. It is to be understood that the bioreactor and the downstream unit are fluidly connected to each other. A pump might be provided for transferring the supernatant into the downstream unit. A preferred embodiment of the cell culture unit C is represented in FIG. 2. The bioreactor 1 comprising the cell culture medium 2 is connected to an internal culture medium tank 3. Said connection is provided by at least one in-tubing 4 and an inlet of the bioreactor 1. Preferably, internal culture medium tank 3 is supplemented with culture medium from an external culture medium container (not represented) which is positioned outside the cupboard-sized system of the invention. Said external culture medium container comprises up to 10 000 L, preferably up to 20 000 L of culture medium which is maintained at room temperature, i.e. about 20° C. The culture medium is preferably pre-heated in the internal culture medium tank 3 to a temperature of about 37° C.

Supplemented culture medium, also herein called supplemented medium, refers to the supernatant of the bioreactor which might comprise culture medium and/or cultured cells and/or their products. The supernatant of the bioreactor might be devoid of cells and/or their products. Cells product refers to biomolecules such as proteins, peptides, produced by the cells and/or any other cell biomolecules derived from cell lysis such as cell membranes.

At least one pump can be provided for ensuring cell medium transfer from the tank 3 to the bioreactor 1. Preferably, the medium transfer is performed continuously and/or at a constant rate and/or at variable rates. Said medium transfer can also be performed discontinuously and/or at a constant rate and/or at variable rates. For connecting the cell culture unit C to a downstream unit or any other unit or device, at least one out-tubing 5 which is attached to an outlet of the bioreactor 1 is provided. A control box 9 might be provided in the cell culture unit C for controlling physical and/or chemical parameters of the supernatant collected from the bioreactor.

The downstream unit may comprise filtration means and/or harvest means and/or dialysis means and/or biomolecules purification means such as proteins or peptides purification. In its most simple form, said downstream unit comprises solely means for harvesting the desired end-product, without any prior filtration/purification/dialysis steps. The components of the downstream unit are easily connected to or disconnected from said unit and can hence be easily replaced, cleaned or sterilized. The downstream unit can be customized depending on the needs and desires of the users, and can be supplied with a combination of any of the aforementioned units. The user is hence provided with multiple end product possibilities, cells, filtered cells, filtered cells products, purified cells products or biomolecules. The user can choose and connect the different compartments of the downstream depending of the desired final product.

In a preferred embodiment, the downstream unit receives supplemented medium or medium supplemented with biomolecules from said bioreactor in continuous mode. Preferably, the downstream unit receives at most 1000 ml/min of medium supplemented with biomolecules from said bioreactor in continuous mode. Preferably, the transfer of the supplemented medium is initiated when a predetermined cell density is reached inside the bioreactor. Said predetermined cell density is at least 30 million/ml, preferably 40 million/ml, more preferably 50 million/ml, most preferably 60 million/ml. In a preferred embodiment, in parallel to the transfer of the supplemented medium from the bioreactor to the downstream unit, culture medium is added from the internal culture medium tank to said bioreactor such as to maintain the initial volume of culture medium in the bioreactor. For instance, if at the start of the process the bioreactor contained 80 L of culture medium, once the transfer of supplemented medium from the bioreactor to the downstream unit is initiated, new culture medium is added to the bioreactor in sufficient volume such as to maintain a volume of 80 L in said bioreactor. If the transfer of supplemented medium from the bioreactor to the downstream unit is performed in continuous mode, the addition of new culture medium from the internal culture medium tank into the bioreactor will be also carried out in continuous mode. The method and the system of the present invention thereby allow the treatment of the supplemented culture medium in the downstream unit in parallel to the growth of the cells in the bioreactor. This provides several advantages compared to processes wherein cells are grown in large bioreactors containing large cell culture volumes followed by stopping said cell culture after a certain time period or when reaching a certain concentration and then starting the downstream processes of the large volume of cell culture. Amongst the advantages we can mention a considerable yield increase and thereby a considerable cost decrease.

In a preferred embodiment, the medium supplemented with biomolecules received by the downstream unit undergoes at least one process selected from the group comprising filtration, harvesting, dialysis, biomolecules purification and protein concentration or any combination thereof.

The supplemented medium harvest is preferably performed in a continuous way at small volume rate. Said volume rate is of at least 100 ml/min, preferably at least 150 ml/min, more preferably at least 200 ml/min, most preferably at least 250 ml/min. Said volume rate is at most 1000 ml/min, preferably at most 800 ml/min, more preferably at most 600 ml/min, most preferably at most 400 ml/min. The supernatant harvest can also be performed in a discontinuous way. The harvested supernatant is then subject to a subsequent treatment selected from simple harvesting, filtering, molecules purification, storage or any combination thereof. The treatment of small volumes of supplemented medium considerably reduces yield loss and improves the treatment quality and efficiency, e.g. better filtration and/or the purification quality. In addition, no scaling up of the operations carried out in the downstream unit is required thereby avoiding spending time and money for scaling up said operations.

The continuous harvest mode of the present invention can be initiated by the operator based on product concentration. The harvest continues until a pre-programmed time interval has passed or until the operator manually terminates the harvesting using a user's interface provided in the system of the invention.

Figure 6:
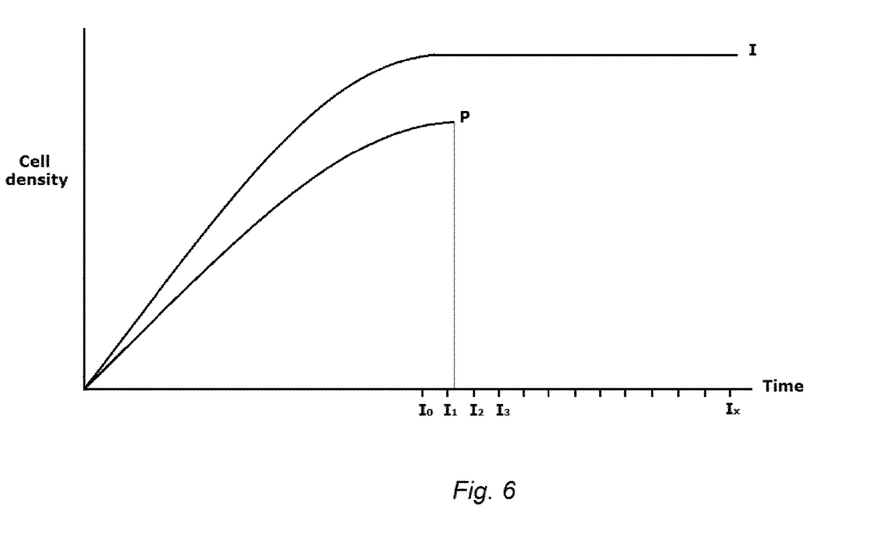
FIG. 6 shows the difference between prior art methods used for biomolecules production and the method of the present invention.

FIG. 6 shows the difference between prior art methods used for biomolecules production and the method of the present invention. In prior art methods, cells are grown for a certain time period or until reaching a certain concentration as shown by curve P of FIG. 6. Afterwards, cell culture is stopped and the downstream processes of the large volume of cell culture can be started and some steps such as clarification should be performed in about 8 hours. As mentioned above, this methodology leads to an important yield loss and is rather expensive. The method of the present invention starts by culturing cells at high density, of at least 50 million cells per ml. Once the required density is reached, cell culture is maintained through time (curve I of FIG. 6) and downstream processing of the supernatant is initiated ($I_0$ in FIG. 6). Said downstream processing is performed on pre-defined amounts of supernatant and is repeated after fixed or non-fixed time intervals ($I_1$ to $I_x$ in FIG. 6). The downstream processing is selected from filtration and/or harvesting and/or dialysis and/or biomolecules purification or any combination thereof. The method of the present invention thereby allows a considerable yield increase, cost decrease while using small equipment's requiring less space and easier to entertain.

In a preferred embodiment, non-disrupted cultured cells are harvested in bulk from the bioreactor into a bag provided in the downstream unit. The cells can be hybridoma cells, transfected or transduced cells or stably transfected cultured cells. In order to get the cells loose from their substrate (the fibers), the bioreactor may be subjected to a discontinuous or a continuous agitation prior to harvesting. Said agitation is from 10 to 150 Hz at amplitude 1-5 mm, preferably from 20 to 100 Hz at amplitude 1-5 mm. In the event the bioreactor is provided with carriers, the agitation will separate the cells from said carriers and bring them into the supernatant. Said carriers might be fibers, microfibers, hollow fibers or hollow microfibers. Alternatively, the carriers can be microbeads in suspension, in packed bed or in fluidized mode. Said carriers provide for an excellent substrate for the cells to grow on. Preferably, the bioreactor comprises microcarriers, by preference polyester microfiber carriers. Harvesting of the supernatant is performed using harvest means comprising at least one pump. The bag and/or the downstream unit can be adapted to maintain the harvested supernatant at the same temperature as the temperature of the culture medium or at a different temperature. The harvested cells might be maintained in the bag of the downstream unit at a temperature of about 4° C. The cultured cells harvested in bulk can be are filtered using filtering means of the downstream unit prior directing said cells into the bag.

In a preferred embodiment, cultured cells are infected and subsequently disrupted/lysed in a thereto designed location in the downstream unit. The supernatant comprising the cell debris and the desired products is then harvested using harvest means from the bioreactor. Harvesting rates are as mentioned above. The supernatant can be harvested and stored for further use into a bag provided in the downstream unit as mentioned above. The harvested supernatant might be subject to a filtration using filtration means prior to storage into a bag of the downstream unit. Alternatively, the collected supernatant can be filtered and/or subject to a purification step for separating a specific molecule, such as an antibody, from said supernatant.

Figure 3:
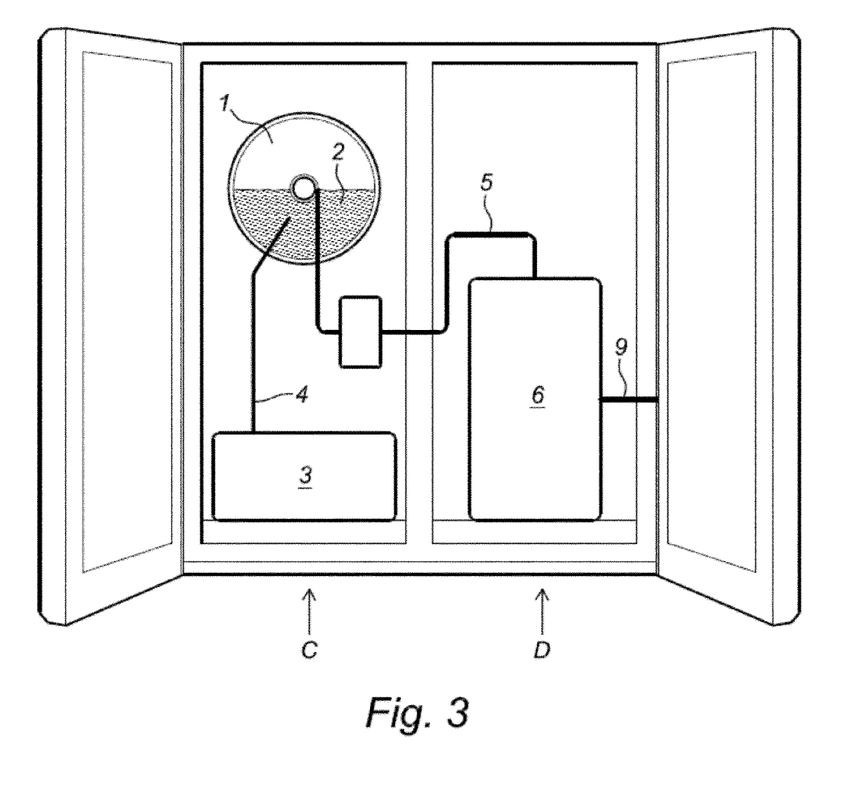
FIG. 3 shows the culture unit C which is fluidly connected to a downstream unit D comprising harvest means according to an embodiment of the invention.

FIG. 3 shows an embodiment of the system which is adapted for harvesting cells or end product in bulk. The culture unit C is fluidly connected to the downstream unit D through the out-tubing 5. The culture unit C is as described above. A pump or harvest means might be provided for collecting the supernatant of the bioreactor. The pump can be programmed such as to start the supernatant collection from a pre-defined time period from the start of the culture. The pump can be programmed such as to collect a pre-fixed volume of supernatant in an automated continuous mode. The collected supernatant is directed to a bag or a collection tank 6 in which said supernatant will be stored for further applications.

Figure 4:
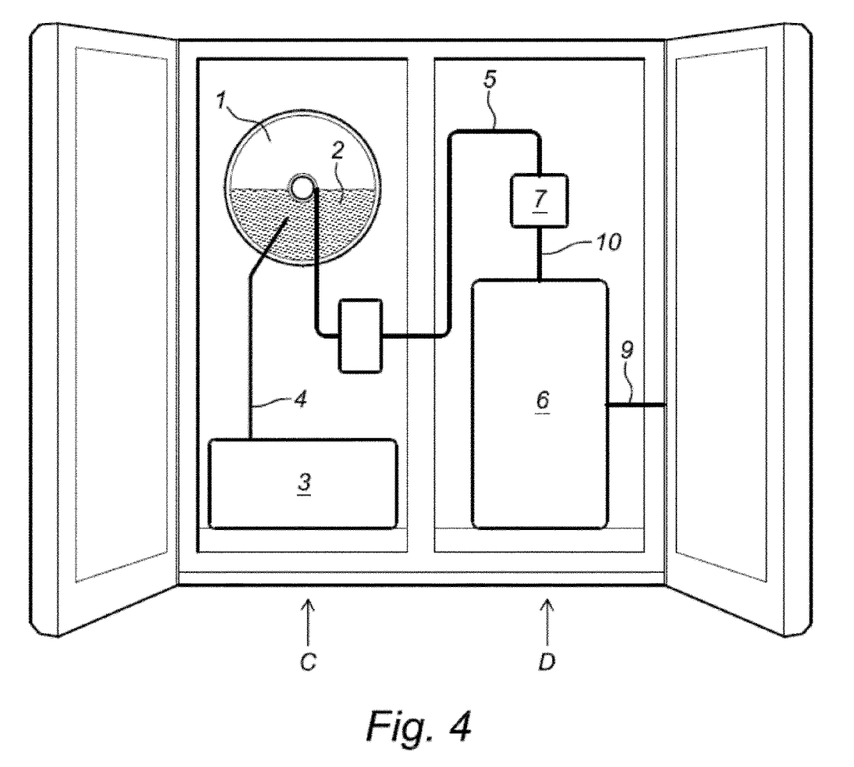
FIG. 4 shows the culture unit C which is fluidly connected to a downstream unit D comprising filtration means and harvest means according to an embodiment of the invention.

FIG. 4 shows an embodiment of the system which is adapted for harvesting and filtering. The culture unit C is fluidly connected to the downstream unit D through the out-tubing 5. The culture unit C is as described above. The out-tubing 5 directs the supernatant to a filtering means 7. A pump, or harvest means, might be provided for collecting the supernatant of the bioreactor. The pump can be programmed such as to start the supernatant collection from a pre-defined time period from the start of the culture. The pump can be programmed such as to collect a pre-fixed volume of supernatant in an automated continuous mode. The collected supernatant is filtered by the filtering means and the filtered supernatant is directed and/or stored into a bag or a collection tank 6 for use in further applications.

Purification can be performed using purification means of the downstream unit. Said means can be automated means for obtaining a purified biological product such as protein (e.g., a purified antibody), from the supernatant (e.g., protein-containing aqueous medium) and harvested as mentioned above. In a preferred embodiment, the purification means comprise at least one or any combination of the following: a selection device such a purification chromatography column (affinity purification, ion exchange, etc.), a sequence of purification columns or membrane absorbers at least one liquid reservoir, a device for flowing liquid from the reservoirs and into the selection device, a device for diverting the effluent from the selection device. The purification means are capable of being installed into the small-scale cupboard-sized system of the invention via a single motion or "snap-on" or "quick-load" technique and comprises mechanical and electrical interfaces for communicating with the other components of the system of the invention. It is to be understood that the required buffers and solutions for performing the purification process or step might be provided in at least one bag. Said bag can be positioned inside or outside the downstream unit and is naturally provided with the necessary connections to ensure its connection with to the purification unit.

Figure 5:
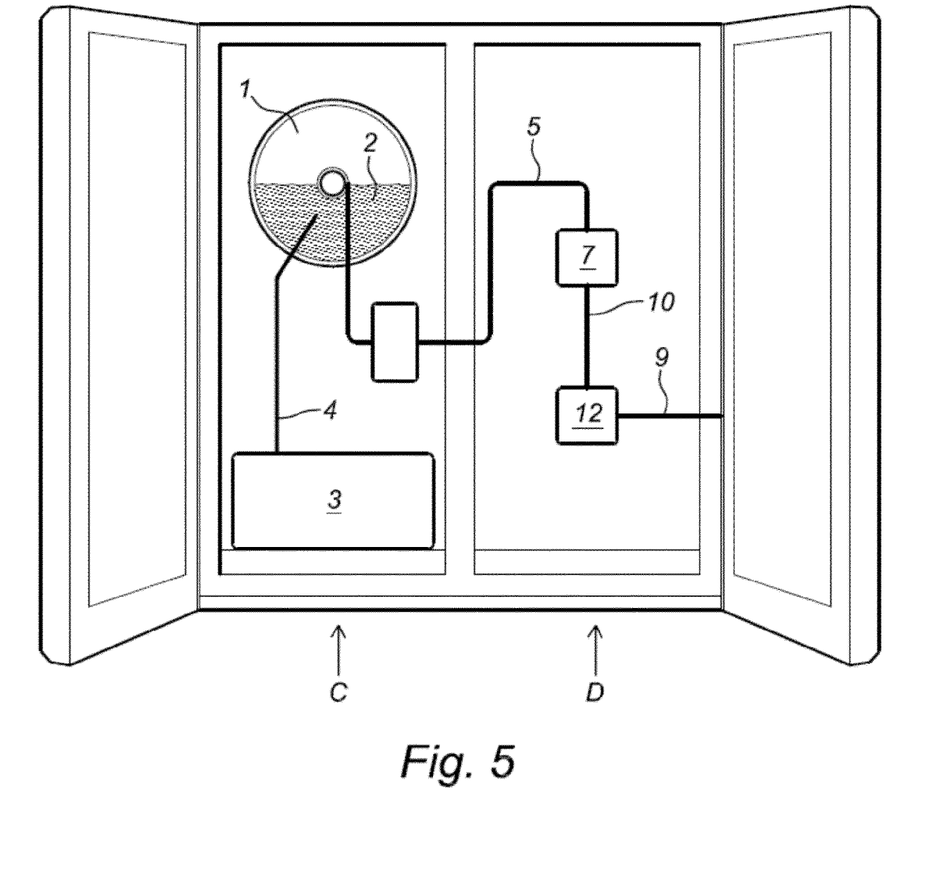
FIG. 5 shows the culture unit C which is fluidly connected to a downstream unit D comprising filtration means and purification means according to an embodiment of the invention.

FIG. 5 shows an embodiment of the system which is adapted for harvesting, filtering and purifying at least one cell product, such as a protein or a peptide. The culture unit C is fluidly connected to the downstream unit D through the out-tubing 5. The culture unit C is as described above. The out-tubing 5 directs the supernatant to a filtering means 7. A pump, or harvest means, might be provided for collecting the supernatant of the bioreactor. The pump can be programmed such as to start the supernatant collection from a pre-defined time period from the start of the culture. The pump can be programmed such as to collect a pre-fixed volume of supernatant in an automated continuous mode. The collected supernatant is then directed to purification means 12 of the downstream unit D. The obtained purified cell product can be stored in a tank connected to the purification means or directed to another component of the downstream for further applications.

The selection device can be a chromatography column such as such as affinity chromatography, ionic exchange chromatography (e.g. anion or cation), hydrophobic interaction chromatography, size exclusion chromatography (SEC), immuno-affinity chromatography which is a column packed with an affinity resin, such as an anti-IgM resin, a Protein A, a Protein G, or an anti-IgG resin. Anion exchange exploits differences in charge between the different products contained in the harvested supernatant. The neutrally charged product passes over the anion exchange chromatography column cartridge without being retained, while charged impurities are retained. The size of the column may vary based on the type of protein being purified and/or the volume of the solution from which said protein is to be purified.

In a preferred embodiment, the purification means, e.g., an affinity column, and/or the filtration means are connected to multiple liquid reservoirs. The reservoirs each contain liquid, such as a wash buffer, an elution buffer, or a neutralization solution, for delivery to the purification means and/or the filtration means. The purification means further comprise pre-sanitized or pre-sterilized device for flowing liquid from the reservoirs into the chromatography column for instance. For example, pre-sterilized valves and tubing which connect the reservoirs to the column might be used.

Purification using a chromatography column is known to the person skilled in the art and can be performed using the adequate buffers for eluting the desired biomolecules. Upon eluting the desired biomolecule, the eluted purified protein can be automatically deposited into a pre-sterilized, disposable collection vessel provided in the downstream unit and removed from the purification means. Alternatively, the eluted purified protein can undergo further automated processing. A purified protein, e.g., antibody, is substantially free from host cell contaminants such as host cell proteins, nucleic acids and endotoxins.

In a preferred embodiment, the eluted protein is transferred to different solutions. The transfer occurs automatically using a pre-sterilized diafiltration module. Diafiltration is the fractionation process that washes smaller molecules through a membrane and keeps molecules of interest in the retentate. Diafiltration can be used to remove salts or exchange buffers. In discontinuous diafiltration, the solution is concentrated, and the lost volume is replaced by new buffer. Concentrating a sample to half its volume and adding new buffer four times can remove over 96% of the salt. In continuous diafiltration, the sample volume is maintained by the inflow of new buffer while the salt and old buffer are removed. At least 99% of the salt can be removed by adding up to seven volumes of new buffer during continuous diafiltration. Specifically, the diafiltration module is used to further purify the protein (e.g., the antibody) and uses the tangential flow filtration principle whereby molecules over 50,000 Daltons (e.g., the antibodies, such as IgG and IgM) cannot pass through the membrane but small molecules, such as buffers, can pass through. Accordingly, the diafiltration module can be used to exchange one buffer for another and is a more efficient substitute for dialysis. Diafiltration can be used to neutralize pH and as a concentration step (to concentrate the cell product).

In a preferred embodiment, the harvest means and/or the filtration means and/or the purification means include at least one monitoring device for monitoring the circulating medium: non-filtered harvested supernatant, filtered supernatant, purified and eluted product, etc. The monitoring device can be a probe or sensor for measuring the conductivity and/or the pH and/or absorbance at a particular wavelength of said circulating medium. One or more pressure sensors may be included for monitoring circulating medium pressure for excessive pressures, or for control of pump speed, e.g., to maintain the pump speed of the harvest means for instance at a desired pressure.

In a preferred embodiment, the system is adapted to the desired product. This means that if cells in bulk are to be provided, the system will comprise a cell culture unit C and a downstream unit D in which at least one collection bag is provided. If filtered cells are to be provided, the system will comprise the cell culture unit and the downstream unit in which filtering means and at least one collection bag are provided. If a specific protein is to be provided, the system will comprise the cell culture unit and the downstream unit in which at least filtering means and purification means are provided.

In a preferred embodiment, the method further comprises the step of measuring physical and/or chemical parameters of the cell culture and/or culture medium. Said parameters are selected from the group comprising temperature, pH, salinity, acidity or any combination thereof. Measurements can be performed on the culture medium before being injected into the bioreactor and/or in the supernatant which is collected from the bioreactor.

In a preferred embodiment, the method and/or the system of the present invention allows a biomolecules, such as monoclonal antibodies, yield increase compared to the conventional methods. Said biomolecules yield is of from 15 to 100 g/L, preferably from 20 to 60 g/L, more preferably from 25 to 50 g/L, even more preferably from 30 to 45 g/L, most preferably from 35 to 40 g/L of bioreactor or any value comprised within the mentioned ranges.

In a preferred embodiment, the method and the system of the present invention are devoid of closed loops or recirculation loops. This means that the supplemented culture medium is not returned to the bioreactor at any stage of the process such as after its passage through the downstream unit. This is advantageous as it considerably reduces contamination risks. Furthermore, this simplifies the setup and the installation of the system thereby reducing costs.

In a second aspect, the present invention provides a system for the production of biomolecules such as proteins or peptides, comprising a cell culturing unit and a downstream unit which are fluidly connected to each other. Said cell culturing unit comprises at least one perfusion bioreactor, which allows growing cells at a density of at least 50 million cells per ml, and supply means for supplying said bioreactor with cell medium and gas or gaseous mixture. The system is characterized in that the bioreactor total volume is at least 10 liters. In a preferred embodiment, the downstream unit is separate from and positioned outside the cell culturing unit.

In a preferred embodiment, the bioreactor allows high density cell growth. Said density is of at least 50 million cells/ml, preferably at least 80 million cells/ml, more preferably at least 100 million cells/ml, most preferably at least 200 million cells/ml. Said density can reach 600, 500, 400 or 300 million cells/ml.

In a preferred embodiment, the bioreactor total volume is at least 10 L, preferably at least 20 L, more preferably at least 30 L, even more preferably at least 40 L, most preferably at least 50 L. The bioreactor total volume is at most 1000 L, preferably at most 900 L, more preferably at most 800 L, even more preferably at most 700 L, most preferably 500 L. In a further preferred embodiment, the bioreactor total volume is at most 400 L, preferably at most 300 L, more preferably at most 250 L, most preferably at most 100 L. The bioreactor total volume and the bioreactor itself according to the invention are smaller compared to the conventional bioreactors used for high cell density culture. This is advantageous in terms of required space for the system and for ease of use.

In a preferred embodiment, the system is implemented in small-scale cupboard which can be a portable chamber or portable clean room. Preferably, the dimensions of the small-scale cupboard are $0.8 \times 1.6 \times 1.8$ m$^3$. The system according to an embodiment of the invention can be placed in a portable clean room. The cell culture unit and the downstream unit are physically separate but designed to be placed together in a portable chamber (e.g., adjacent to one another). Preferably, the cell culture unit and/or the downstream unit can transfer data and coordinate activity with each other using methods known in the art such as a communication port (e.g., an infrared communication port, desktop or laptop computer, etc). The downstream unit can be placed next to the cell culture unit towards the end of the production period, or before. At least one tubing line from each unit fluidly connects said units to each other. The operator initiates the culture process and/or harvesting process and/or the purification process through a user interface such as a touch screen interface on portable chamber and/or the cell culture unit.

By preference, the operating temperature of the cell culture unit is between 20° C. and 40° C., more by preference between 25° C. and 37° C. The operating temperature of the downstream unit may be between 0° C. and 25° C., more preferably between 1° C. and 20° C., even more preferably between 2° C. and 10° C., most preferably about 4° C. The temperature of both units is maintained by cooling and/or warming units and maintenance of the temperature may be checked by sensors.

Integrating components, functions, and operations greatly reduces manpower and cost needed to produce a cells and/or cell-derived product. The integrated system reduces preparation and loading time and reduces the number of operator induced errors which can cause failure. Process sequencing reduces operator time needed and allows sequential operations to be automatically. Modularizing the functions into a cell culture unit and a purification unit allows higher utilization of hardware and lower costs.

The cell culture unit provides for production of cells and cell derived products in a closed, self-sufficient environment. Said unit may comprise at least one bioreactor for cells and/or their products expansion with minimal need for technician interaction. Said bioreactor may be attached to the system in a fixed manner, or may be removably attached to said system.

The bioreactor used in the method and/or the system of the invention can be any type of bioreactor that allows high cell density cultures. Said bioreactor is preferably a perfusion bioreactor. Said bioreactor might be provided with carriers such as fibers, microfibers, hollow fibers or hollow microfibers. Alternatively, those carriers can be microbeads in suspension, in packed bed or in fluidized mode. Said carriers provide for an excellent substrate for the cells to grow on. Preferably, the bioreactor comprises microcarriers, by preference polyester microfiber carriers. Preferably, the microfiber carriers are biocompatible. By preference, they are nonwoven polyester carriers. Following bioreactor inoculation with cells, the cell culture unit follows pre-programmed and automated processes to deliver culture media to the bioreactor and/or maintain pH and/or maintain temperature. Standard or unique cell culture growth parameters can be programmed, such that, various cell types can be expanded and such that cells or cell products can be harvested in an efficient, reproducible manner with minimal chance of human error. In a further preferred embodiment, said carriers have received a plasma treatment in order to make them hydrophilic. The cells will attach to the carriers as a 3D growth substrate. During protein production, the supernatant may become loaded with the desired end product. By supernatant, reference is made to the culture medium which is inside the bioreactor during cell culture which comprises the grown cells and/or the cells product.

Preferably, the carriers present in the bioreactor provide a cell growth surface of at least 1000 square meters ($m^2$), preferably at least 1200 $m^2$, more preferably at least 1500 $m^2$, more preferably at least 1800 $m^2$. The carriers provide a cell growth surface of at most 3000 $m^2$, more preferably at most 2800 $m^2$, more preferably at most 2500 $m^2$, most preferably at most 2200 $m^2$. Preferably, the cell growth surface provided by the carriers is about 2000 $m^2$.

In a preferred embodiment, the bioreactor used in the method and/or the system of the invention is a small size bioreactor. Said bioreactor can be a circular bioreactor having a diameter of at least 30 cm, preferably at least 40 cm and at most 70 cm, preferably at most 60 cm, more preferably at most 50 cm. Said bioreactor can also be a rectangular or square bioreactor having a height of at least 40 cm, preferably at least 50 cm, more preferably at least 60 cm and at most 110 cm, preferably at most 100 cm, more preferably at most 80 cm, most preferably at most 70 cm. The width of said rectangular or square bioreactor is least 40 cm, preferably at least 50 cm, more preferably at least 60 cm and at most 100 cm, preferably at most 90 cm, more preferably at most 80 cm, most preferably at most 70 cm.

The bioreactor can be gyrated or motioned thereby increasing oxygen transfer and ensuring gas equilibrium in said bioreactor. This allows to run cultures in a bioreactor which is devoid of sensors thereby providing a simple and less complicated bioreactor installation compared to the bioreactors of the prior art. In addition, the use of a bioreactor devoid of sensors provides for a considerable decrease of contamination risk. Motioning the bioreactor further improves cells harvesting. Indeed, harvesting cells from a carriers-containing bioreactor, such as fibers or microfibers bioreactors has been difficult to accomplish. Typically, cells are sticky and attach themselves to the carriers or to other cells and form clusters. Motioning the bioreactor forces the cells free thereby providing increased efficiency of cell harvest at high cell viabilities without the use of chemical or enzymatic release additives. The bioreactor may have a rigid or a non-rigid outer body. Rigid outer body allows for the bioreactor case to be flexed causing microfiber movement. This movement enhances the release of cells that have attached to the side of the bioreactor matrix.

Figure 1:
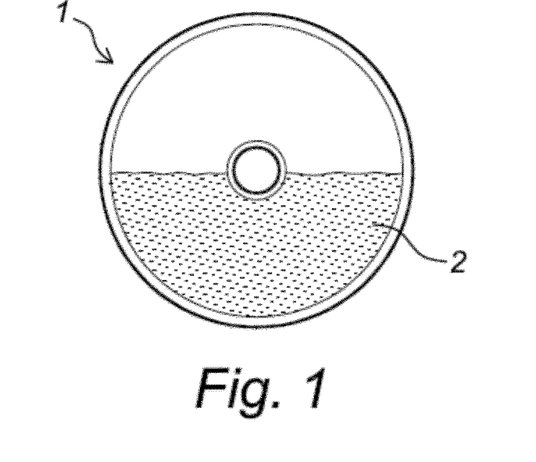
FIG. 1 shows an embodiment of a bioreactor of the invention.

In a preferred embodiment, the bioreactor is a perfusion bioreactor. Preferably, the bioreactor is provided with a single inlet. More preferably, gas and culture medium are introduced into the bioreactor through the same inlet. Perfusion of gas and culture medium into the bioreactor via a single inlet minimizes contamination risks as only one inlet of the bioreactor has to be connected to a perfusion line. In addition, the bioreactor is thereby provided with an easy connection and disconnection system to the perfusion line thereby simplifying its separation from the system if the bioreactor needs to be replaced for instance. An example of bioreactor suitable to be used in the method and/or the system of the invention is represented in FIG. 1. The bioreactor 1 is a perfusion bioreactor having a doughnut shape and is about half filled with culture medium 2 during cell culture.

Preferably, the bioreactor is provided with at least one inlet for the introduction of gas and/or culture medium and at least one outlet for the collection of the culture product and/or the medium contained in the bioreactor. At least one in-tubing is provided for fluidly connecting the bioreactor, via its inlet, to a culture medium tank and/or a gaseous source. At least one out-tubing is provided for fluidly connecting the bioreactor, via its outlet, to a downstream unit and/or any other device.

In a preferred embodiment, the bioreactor is removably connectable to a cell culture medium container. The culture medium is provided into the bioreactor inlet using at least one pump. By preference, the medium is pre-heated to a temperature of between 25° C. to 37° C. and mixed prior to transfer to the bioreactor. This ensures that the cells will not perceive a cold-shock when being contacted with new medium (which would negatively affect their growth) as well as ensure that all nutrients in the medium are mixed and present in the required amounts. The medium can be a liquid comprising a well-defined mixture of salts, amino acids, vitamins and one or more protein growth factors. The culture medium serves to deliver nutrients to the cell and conversely, to remove or prevent a toxic build-up of metabolic waste.

Gas such as pure oxygen or a gaseous mixture comprising oxygen is equally provided through the bioreactor inlet. Oxygen is an essential requirement for the normal growth of mammalian cells. By preference, said gas or gaseous mixture is supplied under pressure. In an embodiment, cells will be exposed to dissolved oxygen concentrations of 300 µM or less (160 mmHg partial pressure), by preference less than 200 µM, most preferably between 20 and 150 µM.

In a preferred embodiment, gas or gaseous mixture and culture medium will be intermixed prior being supplied to the bioreactor. Hence, the mix of gas or gaseous mixture and culture medium are supplied to through one supply line. This gives as an advantage that a cell medium with optimal oxygen concentration is provided directly to the cells. In a further preferred embodiment, said gas or gaseous mixture is chosen from air or oxygen. By preference, air is being used. Air is to be seen as a gaseous mixture, comprising approximately 78% of nitrogen, 21% of oxygen and argon and carbon dioxide. Supply of air instead of pure oxygen or oxygen enriched atmospheres has as an advantage that the system employing the method can be omitted of supplying units of highly concentrated oxygen, which may otherwise imply a fire or explosion hazard.

The low solubility of oxygen in aqueous medium (such as a cell culture medium) relative to its rate of consumption causes its rate of supply to be the limiting factor for cell growth. Generally, the oxygen transfer rate in a fermentor or bioreactor is described by:

$$OTR=K_La(C_{gas}-Ch_{liq}),$$

Whereby OTR=oxygen transfer rate in $\mu mol\ O_2 l^{-1}\ h^{-1}$;
$K_La$=is the oxygen transfer coefficient in $h^{-1}$;
$C_{gas}$=gas-phase $O_2$ (equilibrium) concentration in $\mu M$;
$C_{liq}$=liquid phase $O_2$ concentration in $\mu M$ By preference, the oxygen transfer coefficient ($K_La$) in the current method is at least 20 $h^-$, preferably at least 30 $h^{-1}$, more preferably at least 35 $h^{-1}$. Said oxygen transfer coefficient is at most 100 $h^{-1}$, preferably at most 50 $h^{-1}$, more preferably at most 40 $h^{-1}$.

A high oxygen transfer coefficient and therefore also high OTR will have a positive influence on the cell growth/health and hence the yield of the desired end product. It was found by the inventors of the current method that an oxygen transfer coefficient as defined above is particularly beneficial in terms of product yield, even when making use of a rather small amount of cell starter culture.

In a preferred embodiment, the bioreactor of the system and/or the method of the invention comprise carriers and is subject to motioning. The carriers and the motioning increase in a synergetic way the oxygen transfer coefficient in the bioreactor. Motioning the bioreactor, which is at least partially filled with culture medium, makes part of the carriers travel from a liquid phase, in which they are in contact with the culture medium, to a gas phase, in which they are not in contact with said medium. This increased oxygen transfer rate by at least 10 times compared to bioreactors of the prior art.

In a particular embodiment, the system is provided with necessary and suitable connections for diverting cell culture waste into a waste container.

The bioreactor of the system is fluidly connectable to at least one downstream unit. In a preferred embodiment, the downstream unit comprises pluggable means selected from the group comprising at least one filtration means, at least one harvest means, at least one dialysis means, at least one biomolecules purification means and at least one protein concentration unit or any combination thereof.

In a preferred embodiment, the downstream unit comprises at least one harvest means which is provided with at least one inlet and at least one outlet. Said means of the downstream unit is connectable to the cell culture unit of the system. Preferably the connection is provided by connecting the bioreactor out-tubing to said harvest means. The harvest means comprise at least one tubing for directing the collected supernatant to another component of the downstream unit. The harvest means further comprise at least on pump for withdrawing the supernatant from the bioreactor.

In a preferred embodiment, the downstream unit comprises at least one filtration means which is provided with at least one inlet and at least one outlet. Said means can be fluidly connected to the bioreactor by its out-tubing or fluidly connected to the harvest means of the downstream unit. Preferably, the filtering means comprises a filter that will selectively retain molecules based on their mass in Dalton for instance. The filtration means might comprise virus hollow filters might be used to filter and remove virus particles from the supernatant. In this case, virus filtration works on the principle of size exclusion. When a protein solution with possible viral contamination is introduced into these hollow filters, the smaller proteins penetrate the filter wall and work their way to the outside of the filter while the larger virus particles are retained.

In a preferred embodiment, the downstream unit comprises at least one purification means which is provided with at least one inlet and at least one outlet. Said means can be fluidly connected to the bioreactor by its out-tubing or fluidly connected to the harvest means or the filtration means of the downstream unit. Preferably, the purification means comprises at least one selection de vice as described earlier.

In a preferred embodiment, the system comprises a cell culture unit and a downstream unit. The cell culture unit comprises at least one bioreactor for culturing cells. Said bioreactor is connected to a culture medium tank for receiving culture medium. For connecting the cell culture unit to a downstream unit or any other unit or device, at least one out-tubing attached to an outlet of the bioreactor is provided. Said out-tubing is suitable to be connected to the harvest means inlet, filtering means inlet or purification means inlet of a downstream unit thereby fluidly connecting both units to each other. In a further preferred embodiment, the bioreactor out-tubing is connected to the harvest means inlet. The harvest means outlet is connected to a filtration means inlet and the filtration means outlet is connected to the purification means inlet.

The person skilled in the art will appreciate that necessary tubing and/or pump can be provided within the system for achieving the fluid connection between the different compartments of the cell culture unit and/or of the downstream unit. Further, the system can be provided with a plurality of switch valves used to route the fluids between said different compartments. In addition, a software program for running the system and the method according to an embodiment of the invention can be provided.

The method and/or the system of the present invention can be used for the culture of any cell line and/or for the production of any desired protein and peptide. Possible cultured cell lines are the Vero cells, the CHO cells, COS cells, 293T cells, HeLa cells, Hep-2 cells, MCF-7 cells, U373 cells or any other cell line.

The method and system according to the current invention is particularly useful for the production of biosimilar antibodies. The term 'biosimilar' antibodies is to be understood as 'generic' versions of 'originator' antibodies which have the same amino acid sequence as those 'originator' antibodies but which are produced from different clones and/or by different manufacturing processes.

The method and/or the system can be used for the production of:
Anti-inflammatory biomolecules or any antibody such as infliximab, adalimumab, basiliximab, daclizymab, omalizumab, palivizumab and abciximab
Anti-cancers biomolecules such as gemtuzumab, alemtuzumab, rituximab, transuzumab, nimotuzumab, cetuximab, bevacizumab.

It is supposed that the present invention is not restricted to any form of realization described previously and that some modifications can be added to the presented example of fabrication without reappraisal of the appended claims.

The invention is further described by the following non-limiting examples which further illustrate the invention, and are not intended to, nor should they be interpreted to, limit the scope of the invention.

EXAMPLES

Example 1

Manufacturing of an RSV-Antibody Based Vaccine

The methodology and system of the invention can be used for the production of an RSV-antibody based vaccine, preferably, liquid formulations of a humanized monoclonal antibody which neutralizes a broad range of RSV (Respiratory syncytial Virus) isolates. In particular, the current invention may be used to produce liquid formulations of SYNAGIS®, or an antigen-binding fragment thereof.

The amino acid sequence of SYNAGIS® is disclosed, e.g., in Johnson et al., 1997, J. Infectious Disease 176:1215-1224, and U.S. Pat. No. 5,824,307. The properties and uses of SYNAGIS® are also disclosed in, e.g., other applications, see, e.g., U.S. patent application Ser. No. 09/724,396 filed Nov. 28, 2000; U.S. patent application Ser. No. 09/996,265 filed Nov. 28, 2001 and U.S. patent application Ser. No. 10/403,180 filed Mar. 31, 2003, all of which are incorporated herein by reference.

The methods for preparing liquid formulations of the present invention comprise:

cultivating cells, by preference CHO cells according to the method and system of the current invention. The method may include use of a stable cell line expressing the desired antibody or by making use of a viral vector system;

purifying the antibody from conditioned medium by chromatography;

and concentrating a fraction containing the purified SYNAGIS® to a final antibody concentration of from about 15 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 150 mg/ml, about 200 mg/ml, about 250 mg/ml, or about 300 mg/ml using a semi-permeable membrane with an appropriate molecular weight (MW) cutoff (e.g., 30 kD cutoff for whole antibody molecules and F(ab')2 fragments; and 10 kD cutoff for antibody fragments, such as Fab fragments) and diafiltrating the concentrated antibody fraction into the formulation buffer using the same membrane.

The liquid formulations comprising the antibody can be prepared as unit dosage forms by preparing a vial containing an aliquot of the liquid formulation for a one-time use. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of SYNAGIS® or an antigen-fling fragment thereof ranging from about 15 mg/ml to about 300 mg/ml concentration of SYNAGIS® or an antigen-binding fragment thereof which immunospecifically binds to a RSV. If necessary, these preparations can be adjusted to a desired concentration by adding a sterile diluent to each vial.

The liquid formulations of the present invention may be sterilized by various sterilization methods, including sterile filtration, radiation, etc. In a most preferred embodiment, the diafiltrated antibody formulation is filter-sterilized with a presterilized 0.2 or 0.22-micron filter. Sterilized liquid formulations of the present invention may be administered to a subject to prevent, treat, manage or ameliorate a RSV infection or one or more symptoms thereof.

For the purpose of equivalents the formulations may be lyophilized if desired. Thus, the invention encompasses production of lyophilized forms of the formulations.

The current example may also be applied to other well-known antibody-based formulations such as, but not limiting infliximab, adalimumab, basiliximab, daclizymab, omalizumab, gemtuzumab, alemtuzumab, rituximab, transuzumab, nimotuzumab, cetuximab, bevacizumab, abciximab.

What is claimed is:

1. A system of producing antibodies and vaccines, comprising:
    a cell culturing unit and a downstream unit which are fluidly connected to each other, said cell culturing unit comprises at least one perfusion bioreactor, which allows growing cells at a density of at least 50 million cells per ml, and a supplier is configured to supply said perfusion bioreactor with a cell medium and a gas or gaseous mixture, wherein a total volume of the perfusion bioreactor is in a range of 10 to 900 liters; and
    a single supply line that provides the cell medium and the gas or gaseous mixture to the perfusion bioreactor;
    wherein said system is implemented in a portable chamber, suitable for a portable clean room.

2. The system according to claim 1, wherein the total volume of the perfusion bioreactor is in a range of 10 to 800 liters.

3. The system according to claim 1, wherein said bioreactor further includes carriers.

4. The system according to claim 3, wherein said carriers provide a cell growth surface of at least 1000 m2.

5. The system according to claim 1, wherein said downstream unit comprises at least one element that is fluidly connectable with the perfusion bioreactor via a pluggable connection, said element being selected from the group consisting of a filter, a harvest, a dialyser, a biomolecule purifier and one protein concentration unit.

6. The system according to claim 1, wherein the total volume of the bioreactor is in a range of 10 to 700 liters.

7. The system according to claim 1, wherein the total volume of the bioreactor is in a range of 10 to 500 liters.

8. The system according to claim 1, wherein the perfusion bioreactor does not include any port that provides the addition of the gas or gaseous mixture to the perfusion bioreactor apart from the single supply line.

9. A system of producing antibodies and vaccines, comprising:
    a cell culturing unit and a downstream unit which are fluidly connected to each other, said cell culturing unit comprises at least one perfusion bioreactor, which allows growing cells at a density of at least 50 million cells per ml, and a supplier is configured to supply said perfusion bioreactor with a cell medium and a gas or gaseous mixture, wherein a total volume of the perfusion bioreactor is in a range of 10 to 900 liters; and
    a single supply line that provides the cell medium and the gas or gaseous mixture to the perfusion bioreactor;
    wherein the system is devoid of a recirculation loop.

* * * * *